(12) United States Patent
Giridhar

(10) Patent No.: US 8,906,696 B2
(45) Date of Patent: Dec. 9, 2014

(54) DEFORMABLE POLYMER TESTING DEVICE

(75) Inventor: Archit Giridhar, Singapore (SG)

(73) Assignee: STMicroelectronics Asia Pacific Pte Ltd, Singapore (SG)

( * ) Notice: Subject to any disclaimer, the term of this patent is extended or adjusted under 35 U.S.C. 154(b) by 265 days.

(21) Appl. No.: 13/593,319

(22) Filed: Aug. 23, 2012

(65) Prior Publication Data

US 2014/0057808 A1 Feb. 27, 2014

(51) Int. Cl.
*G01N 1/10* (2006.01)
*C12M 1/34* (2006.01)
*C12M 3/00* (2006.01)
*C12Q 1/68* (2006.01)

(52) U.S. Cl.
CPC . *C12M 1/34* (2013.01); *C12M 3/00* (2013.01); *B01L 2300/041* (2013.01); *C12Q 1/686* (2013.01); *B01L 2300/042* (2013.01); *B01L 2300/043* (2013.01); *B01L 2300/044* (2013.01); *B01L 2300/045* (2013.01); *B01L 2300/046* (2013.01); *B01L 2200/16* (2013.01); *B01L 2200/141* (2013.01); *B01L 2200/142* (2013.01)
USPC ........... 436/165; 422/502; 422/430; 422/547; 422/552; 422/569; 435/285.2; 435/288.4; 435/305.2; 435/305.3; 435/305.4

(58) Field of Classification Search
CPC .......... B01L 2200/16; B01L 2200/141; B01L 2200/142; B01L 2300/041–2300/046; C12Q 1/686; C12M 1/34; C12M 3/00
USPC .......... 422/430, 502, 547, 552, 569; 436/165; 435/284.2, 288.4, 305.2, 305.3, 305.4
See application file for complete search history.

(56) References Cited

U.S. PATENT DOCUMENTS 7,070,740 B1 * 7/2006 Matson et al. ................ 422/552
7,384,779 B2 * 6/2008 Fang et al. ................. 435/287.1
2007/0292837 A1 * 12/2007 Deutsch et al. .................. 435/4

\* cited by examiner

*Primary Examiner* — Lyle Alexander
(74) *Attorney, Agent, or Firm* — Seed IP Law Group PLLC

(57) ABSTRACT

A testing device uses a selectively deformable substrate to capture and retain spherical beads for genetic experimentation. A method of fabricating the device is described in which a silicon substrate can be coated with a photosensitive, biocompatible polymer for photolithographic patterning using a single mask exposure. The polymer is patterned with a matrix of wells, each well capable of expansion to accept placement of a bead in the well, and contraction to secure the bead in the well. The polymer can exhibit piezoelectric properties that cause it to respond mechanically to a selected electrical excitation.

22 Claims, 7 Drawing Sheets

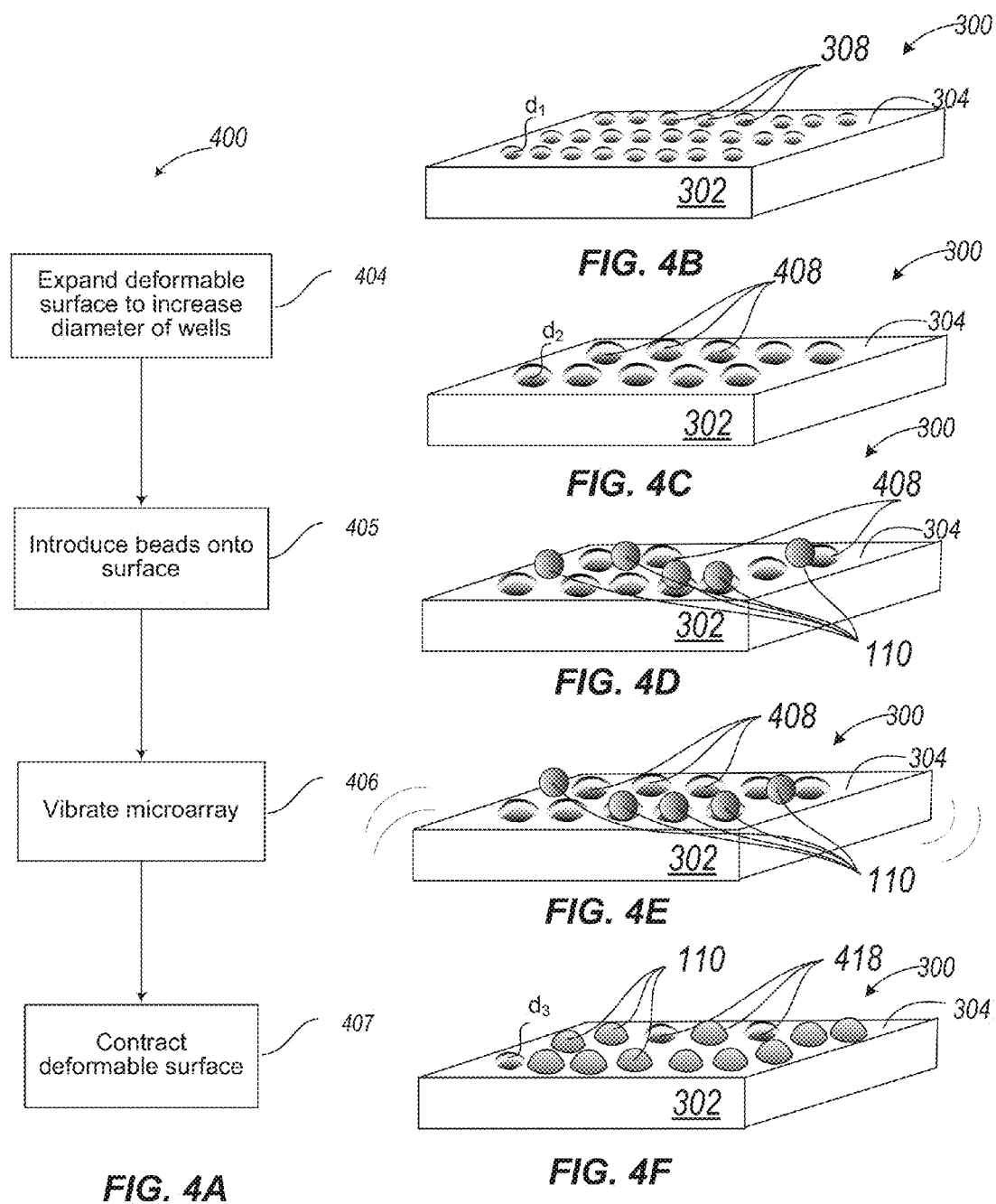

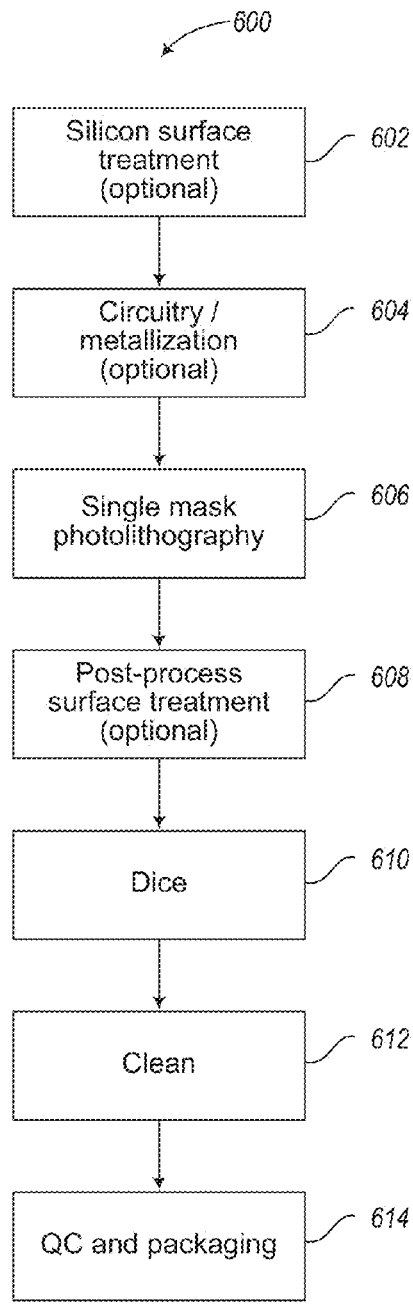
FIG. 6A
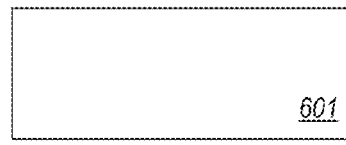
Fig. 6B
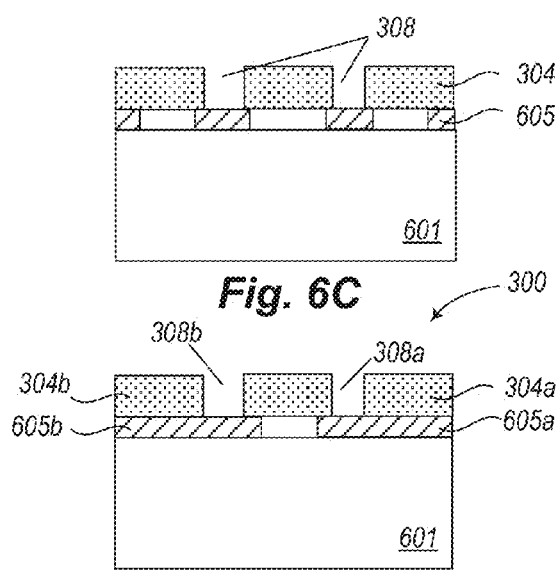
Fig. 6C
Fig. 6D
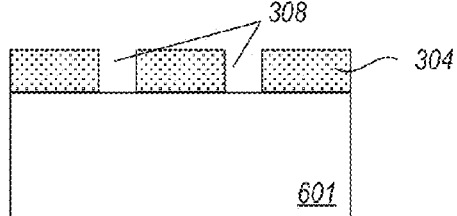
Fig. 6E

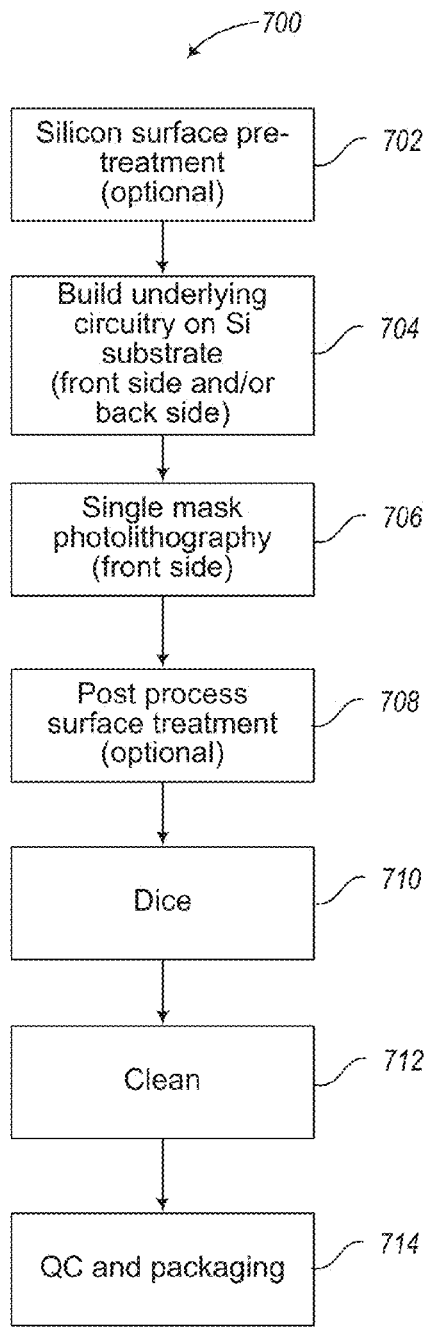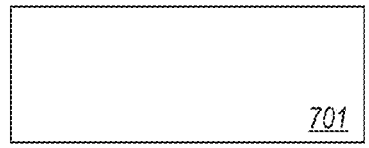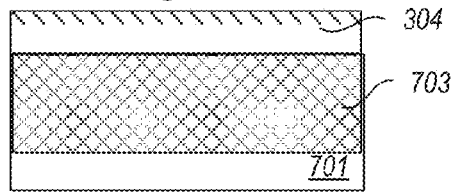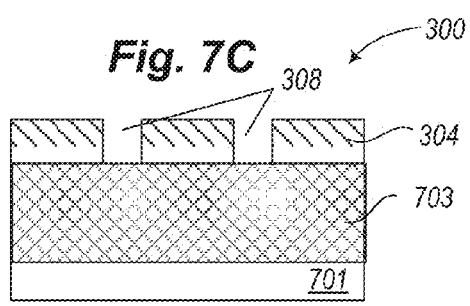
*Fig. 7B*
*Fig. 7C*
*Fig. 7D*
*FIG. 7A*

DEFORMABLE POLYMER TESTING DEVICE

BACKGROUND

1. Technical Field

The present disclosure relates generally to the fabrication and design of polymer substrates that are photo-sensitive and therefore can be patterned using photolithography, and in particular, to testing media used for DNA and RNA hybridization and evaluation.

2. Description of the Related Art

A DNA bead-type microarray is a solid platform having a top surface in which an array (typically a 2-dimensional grid) of wells is formed to support DNA samples for genetic experimentation and analysis. The DNA samples can be attached to spherical beads that fit into hemispherical- or cylindrical-shaped wells. The bead surfaces are engineered with a chemical matrix to which DNA proteins can attach by covalent bonding. Single helical strands of synthesized DNA (i.e., DNA fragments) called probes can therefore be loaded onto a set of beads. Then, genetic samples, or targets, also single helical strands of DNA, carrying chemiluminescent markers, can be introduced to the probes to determine which of the target genes bind strongly with the probe genes. Strongly bonded, or "hybridized" pairs of genes, form a fully complimentary double helix structure. A subsequent washing step clears away weakly bonded, or non-hybridized, pairs, leaving behind the hybridized pairs of genes. The hybridized genes, now carrying the markers, can then be scanned and imaged for evaluation.

Use of bead-type microarrays entails placing the beads into the wells and retaining them in place during the hybridization procedure, the subsequent washing step, and the imaging step. Consistent fabrication of the substrate and the beads is necessary to properly control DNA and RNA hybridization experiments. Typically, the top surface of the microarray is made of a rigid material such as glass; commonly used materials for the beads are silica, zirconium, polystyrene, or glass. The beads and the wells typically have a diameter within the range of about 0.5-1.0 micron, and rows of wells in a microarray are typically spaced about one micron apart. The volume of one of these tiny wells can be on the order of a femtoliter ($1.0 \times 10^{-15}$ liter).

One problem that arises when using microarrays is that many of the beads are not correctly placed or centered in the wells. A common method used to place the beads into the wells is to introduce beads onto the surface of the microarray within a fluid, and rock the array back and forth until the fluid pushes the beads into the wells. This method tends to be tedious and ineffective, typically resulting in only about 70% of the beads seating correctly in the wells. Another problem is that the washing step tends to lift about 5-10% of the beads back out of the wells. Therefore, what is needed to improve the yield and efficiency of DNA experiments is a DNA microarray that can successfully capture and retain close to 100% of the beads in the wells.

BRIEF SUMMARY

A testing device facilitates uniform loading of beads into a matrix of wells to support nucleic acid hybridization or related biomedical experiments. A selectively deformable substrate features a flexible, polymeric surface that is both bio-compatible, and capable of being manipulated mechanically in a controlled fashion. The polymeric surface is capable of expansion to increase a diameter of the wells, and contraction to secure the beads in the wells. In one embodiment, if the polymer used is selected, or engineered, to have certain piezoelectric properties, then the mechanical expansion and contraction of the wells can be controlled by electrical excitation. Furthermore, in a second embodiment, if the testing device is made with an additional layer of metallization adjacent to the piezoelectric polymer, different areas of the polymer can be accessed and energized differently, according to programmed instructions. Alternatives to use of a piezoelectric material include piezomagnetic or piezo-optical materials which respond in a similar fashion, causing deformation of the polymer in response to a magnetic field, or optically responsive upon exposure to certain wavelengths of light, instead of in response to passing a current through the material.

According to a conventional process for building microarrays on a silicon substrate, a rigid surface is created by forming an oxide layer and etching an array of wells into the oxide. According to a fabrication method disclosed herein, a photo-sensitive polymer, which shares some properties of a photoresist, is itself patterned with an array of wells. In this fabrication method, formation of an oxide layer is not necessary, thus increasing efficiency and decreasing the cost of fabrication. The polymer may be optionally processed with pre- or post-lithography surface treatments to adjust relevant bio-compatibility characteristics, such as, e.g., porosity, water-repellency, and adhesion, as needed to facilitate different bio-experimental conditions.

BRIEF DESCRIPTION OF THE SEVERAL VIEWS OF THE DRAWINGS

FIGS. 4A-4F show a sequence of steps and corresponding side views in a method of loading beads into an array of wells formed in a selectively deformable surface, as taught herein.

FIGS. 6A-6E show a sequence of steps and corresponding side views illustrating a first method of fabricating a selectively deformable array as taught herein, according to an alternative embodiment.

FIGS. 7A-7D show a sequence of steps and corresponding side views illustrating a second method of fabricating a selectively deformable array as taught herein, according to an alternative embodiment.

DETAILED DESCRIPTION

It will be appreciated that, although specific embodiments of the present disclosure are described herein for purposes of illustration, various modifications may be made without departing from the spirit and scope of the present disclosure. Accordingly, the present disclosure is not limited except as by the appended claims.

In the following description, certain specific details are set forth in order to provide a thorough understanding of various aspects of the disclosed subject matter. However, the disclosed subject matter may be practiced without these specific details. In some instances, well-known structures and methods of DNA experimentation involving microarrays, or silicon chip fabrication, that comprise embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to microarrays refers to arrays of microscopic locations on a surface, and can include arrays of microscopic structures formed in or on the surface. The term array should be broadly construed to cover at least one-dimensional (linear) arrangements, and two-dimensional (area/matrix) arrangements.

In the figures, identical reference numbers identify similar features or elements. The sizes and relative positions of the features in the figures are not necessarily drawn to scale.

Figure 1:
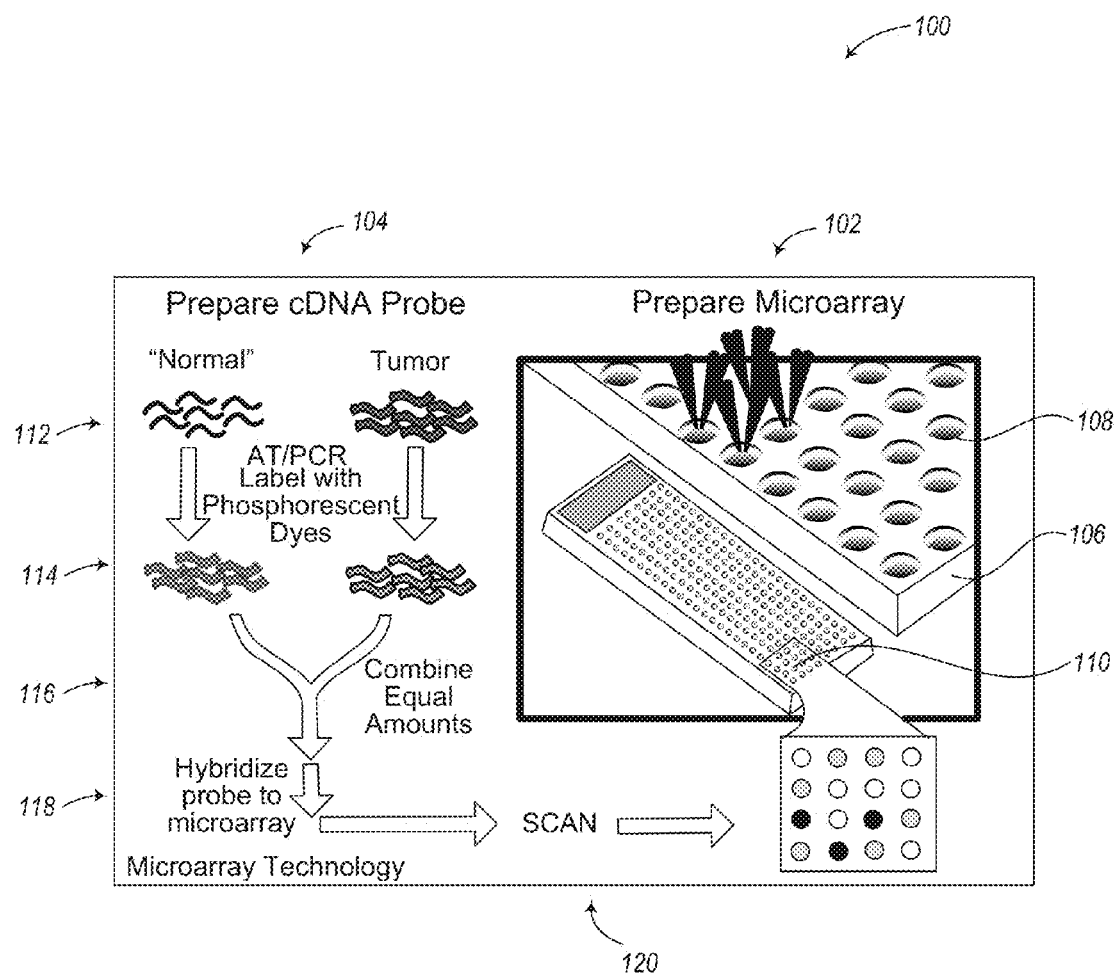
FIG. 1 illustrates a procedure for processing DNA samples, and an existing DNA microarray used as a device for such processing.

With reference to FIG. 1, an exemplary experimental procedure 100 for processing nucleic acid samples using a microarray is illustrated, in accordance with known experimental methods widely used for DNA- and RNA-related studies. The experimental procedure 100 includes a conventional microarray preparation procedure 102 and a DNA probe synthesis procedure 104. The conventional microarray preparation procedure 102 includes obtaining a microarray platform 106, typically including a silicon substrate, having a rigid top surface in which is formed a two-dimensional array, or matrix, of wells 108, and loading the wells 108 with beads 110. The DNA probe synthesis procedure 104 begins with an isolation step 112, in which DNA fragments (e.g., single helical strands) to be used as experimental probes (i.e., known controls), are obtained. In the two-color microarray experiment example shown, DNA probes are isolated from normal cell tissue, and from comparison cell tissue, such as from cancer cells obtained from a tumor. In a labeling step 114, the DNA fragments are labeled, for later identification, with fluorescent, phosphorescent or chemiluminescent dyes. In the two-color example shown in FIG. 1, the normal DNA fragments can be identified by a first dye color, and diseased DNA fragments can be identified by a second dye color, so that later post-analysis of the experiment can reveal which type of the DNA probes bonded more strongly with the DNA targets.

In a combining step 116, the two differently-labeled DNA probe fragments are combined, and in a bonding step 118, the combined DNA probe fragments are chemically attached to a bead 110 for loading into a well 108 in the microarray platform 106. Chemical attachment of DNA probe fragments to a bead 110 having a solid surface can be accomplished by engineering the surface of the bead, which can entail treatment with a chemical matrix so that the DNA fragments will cling to it. Such chemical treatments can include, for example, epoxy-silane, amino-silane, lysine, or polyacrylamide, to which proteins in the DNA probes can bond covalently. Beads prepared in this way can be then be immersed in a sample containing the combined DNA probe fragments, to allow the chemical bonding process to occur.

Once the DNA probes are fixed in place in the microarray platform 106, the platform can be loaded into an automated, pre-programmed machine for further processing, during which DNA sample target fragments, e.g., single helical strands, can be introduced to the DNA probes for hybridization and evaluation. Hybridization refers to a property of nucleotide acid, e.g., DNA or RNA, sequences to form hydrogen bonds between complementary base pairs, which bonds form the cross members of the recognizable double-helix hybridized DNA structure. Washing the microarray following hybridization clears away the weakly bonded, partially complimentary, DNA strands, leaving the strongly bonded, fully complimentary, strands for analysis. Results of the experiment can then be determined by scanning the microarray in a scanning step 120, using a laser beam to look for presence of the luminescent markers indicating which type of probe the DNA target has bonded with. Statistical analysis of the scan data can then be used to draw experimental conclusions.

Many different types of DNA experiments can be carried out using microarrays in this fashion. Some examples include gene expression profiling, genotyping, re-sequencing of mutant genomes, genetic identification of organisms, forensic DNA analysis, identification of drug candidates, measuring predisposition to diseases, alternative splicing detection, and the like. Because microarrays can accommodate, for example, tens of thousands of probes in a single experimental run, they allow many tests to be carried out in parallel, with automated scanning and statistical analysis. The management and processing of the large volume of data produced by microarray experiments has helped to establish a whole new field of research that combines statistics with biology, called bioinformatics. Microarrays are particularly advantageous when used in multi-factorial statistical experiments, which investigate the effects of different factors, as well as possible interactions of the factors, all at one time. Improvements in microarray technology therefore offer the potential to greatly increase the rate of progress of genetic research.

The term microarray includes any arrangement of microscopic locations on a solid surface. Bead-type microarrays are one of at least several different types of microarrays to which the fabrication techniques taught herein may also apply. The present focus is on fabricating the platform itself and on formation of wells in the platform. Although the selectively deformable array disclosed herein is especially well-suited for capturing and retaining spherical beads, applications thereof are not so limited. For example, a deformable array could also be used to secure test vehicles other than beads, e.g., silicon biochips that are also commonly used with microarrays.

Figure 2:
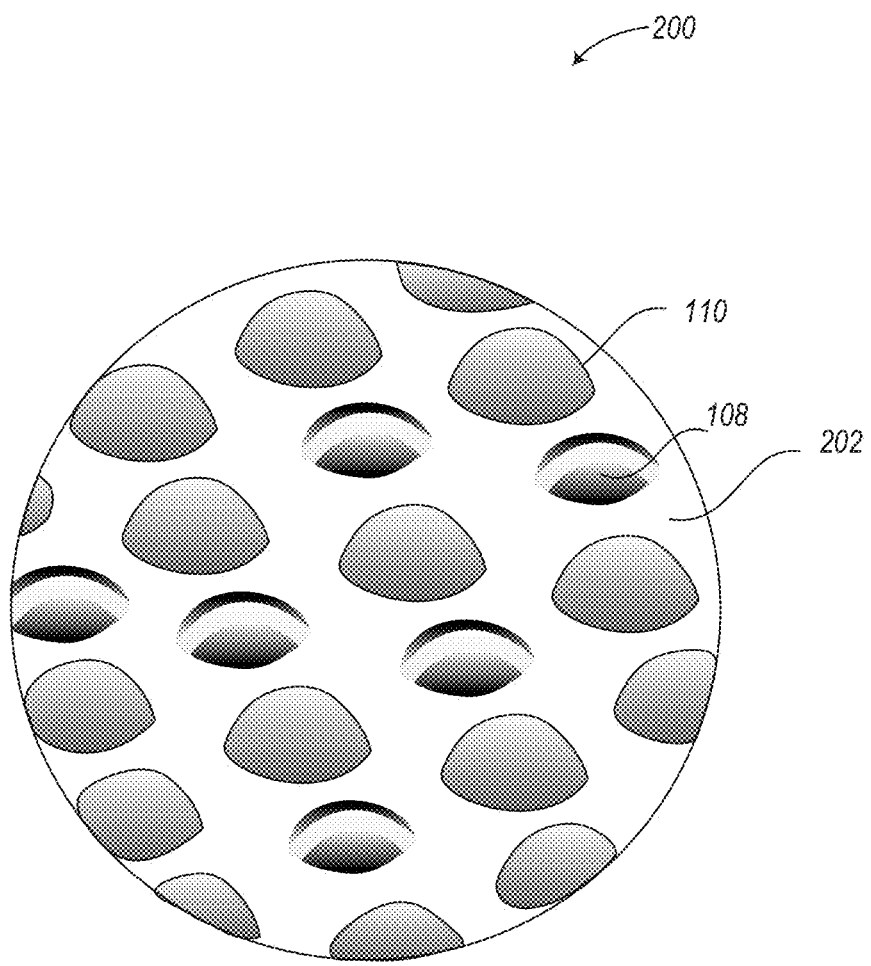
FIG. 2 is a pictorial view of a plurality of beads partially loaded into wells of a prior art microarray such as that shown in FIG. 1.

FIG. 2 shows a magnified partial view 200 of the prior art microarray platform 106, wells 108, and beads 110, after the beads 110 have been loaded, but prior to attaching DNA probes. The top surface 202 of the microarray platform 106 is typically made of a low-friction, rigid material such as silicon, silicon dioxide, or glass. The beads 110 can also be made of a rigid material like glass, or alternatively, a deformable material such as polystyrene, e.g., Styrofoam™. As FIG. 2 illustrates, many of the wells in the rigid microarray platform 106 are not successfully filled with the beads 110. To the extent that some of the wells 108 remain, or later become, unoccupied, the efficiency of subsequent genetic experiments is reduced.

Wells can remain unoccupied because a) the diameter of the beads is too large, causing the bead to roll out or lift out of the well, b) the diameter of the bead is too small, causing it to fall into the well so that it cannot protrude above the top surface 202, c) during the loading step none of the beads were in close enough proximity to the empty wells to be captured, or d) use of a liquid medium to distribute the beads on the surface interferes with their placement in the wells by either filling the wells with liquid, or causing the beads to float. Retention of beads in the wells 108 formed in the rigid microarray platform 106 may be poor because the top surface 202 has insufficient mechanical friction to hold the beads in place once they are seated. Otherwise, effective bead loading largely depends on the relative sizes of the beads and the wells, and the relative density of the beads and the liquid medium. Successful capture and retention of beads using a rigid microarray platform 106 therefore is at least partly dependent on the population of beads having a uniform diameter and density, and the population of wells also having a uniform diameter, as well as movement of the microarray platform 106 during the bead loading step.

Figure 3:
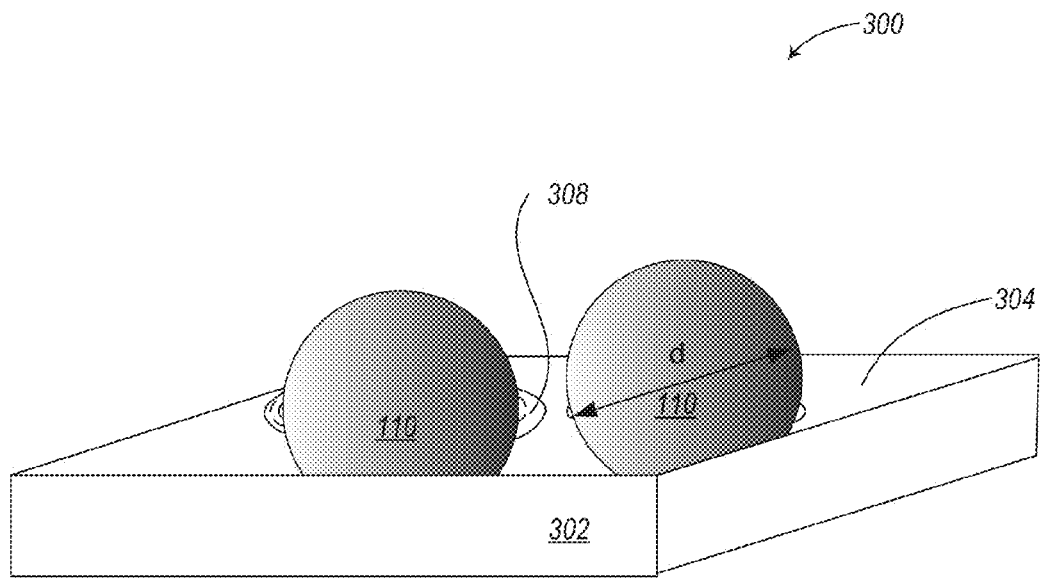
FIG. 3 shows a pair of beads placed on a deformable polymeric surface of a selectively deformable substrate.

Various methods have been proposed to achieve uniform bead loading using the rigid microarray platform 106. These include chemical, thermal, electrical, and magnetic solutions that can introduce additional forces to direct the beads into the wells. These solutions have had limited effectiveness, partly because a rigid microarray platform 106 does not respond very easily to these measures. FIG. 3 illustrates another method of achieving uniform bead loading that employs a testing device 300, suitable for genetic experimentation, the testing device having a selectively deformable substrate 302. According to one embodiment, the selectively deformable substrate 302 includes a bulk substrate, and a selectively deformable surface 304. The substrate 302 differs from the substrate 106 in that the substrate 302 is selectively deformable because the surface 304 is made to be responsive to application of additional forces, whereas the conventional top surface 202 is not.

Embodiments of the testing device 300 can vary considerably while remaining within the scope of the present disclosure. In some embodiments, the bulk substrate on which the selectively deformable surface 304 is formed is made of silicon, but it may be made of, or may include, other materials that could be either rigid or deformable. For example, the selectively deformable substrate 302 need not include silicon per se. There are many other choices for the bulk material of the selectively deformable substrate 302, including for example, silicon-germanium, and III-V semiconductor materials that are commonly processed or patterned with photo-sensitive polymers. Furthermore, the bulk of the substrate may itself be a piezoelectric or otherwise deformable material. For example, in some embodiments, the bulk substrate material can be the same as, or similar to, the selectively deformable surface material. Furthermore, a bulk substrate made of silicon or another rigid material may later be detached, or de-laminated, from the selectively deformable surface 304, once the surface 304 is formed.

Although the embodiments presented herein describe application of electrical forces, the selectively deformable surface 304 is not so limited. Depending on its material properties, the selectively deformable surface 304 can be driven by other, non-electric forces, e.g., chemical, thermal, and magnetic forces. The selectively deformable surface 304, as described herein, in addition to being deformable, is also bio-compatible and photosensitive. In this context, a bio-compatible surface is a surface that does not participate in, or interfere with, chemical or biological reactions that involve the DNA probes or targets as subjects of experimental bio-processing. Use of a photosensitive polymer for the selectively deformable surface 304 is advantageous because it lends itself to patterning using photolithography techniques. A patterned matrix of expandable wells 308 formed in a polymeric selectively deformable surface 304 is then capable of expansion to accept placement of the beads 110, and capable of subsequent contraction to secure the beads 110 in the expandable wells 308.

According to one embodiment of the testing device 300, the material used to make the polymeric selectively deformable surface 304 has piezoelectric properties, so that controlled deformation, e.g., expansion of a well, can occur in response to a selected degree of electrical excitation of the material, e.g., in the vicinity of the well. A material that is simultaneously bio-compatible, photosensitive, and piezoelectric can be made by dispersing nanocomposite elements, e.g., zinc oxide, into a photo-resist-type polymer. One example of an available polymer into which the nancomposites, such as zinc oxide, can be dispersed is SU-8, a common epoxy-based negative photo-patternable polymer. Thus, the selectively deformable property of the polymeric surface 304 is not brought about by simply using a flexible material. In addition to being flexible, to be selectively deformable, the material is made responsive to additional forces because it incorporates elements, such as the nanocomposites, that are capable of sensing and reacting to the additional forces.

In some embodiments, a signal transmission layer underneath the polymeric surface allows for tailoring the degree of electrical excitation to different wells or groups of wells within the matrix. The signal transmission layer can be, for example, a patterned layer of metallization adjacent to the polymer, which allows for addressing different sub-matrices of wells. For example, different sub-matrices of wells can be loaded with different types of beads that can respond to different levels of programmed electrical excitation. The different types of beads may, for example, be made of different materials, or they may be treated with, for example, different bio-agents or reacting specimens.

Because the deformable substrate 302 is pliable compared with the rigid platform 106, the substrate 302 can be manipulated during the loading process so as to encourage more beads 110 to seat properly in, and to stay seated within, the expandable wells 308, according to the loading procedure described below. Use of the deformable substrate 302 can accommodate some variation in the diameters of the beads 110 and the wells 308 because manipulation of the substrate causes the wells to clamp down on, or hug, the bead more securely.

FIGS. 4A, 4B, 4C, 4D, 4E, and 4F show how use of a testing device 300 having a selectively deformable substrate 302 can improve the loading uniformity of beads 110 into expandable wells 308. FIG. 4A shows a sequence of steps in a loading procedure 400 that can be used to load beads 110 into a matrix of expandable wells 308 formed in the selectably deformable substrate 302. FIGS. 4B, 4C, 4D, 4E, and 4F show a sequence of perspective views of the selectably deformable substrate 302 during progression of the loading procedure 400. FIG. 4B shows the testing device 300 prior to the loading procedure 400. Prior to loading, the expandable wells 308 have a selected first well diameter $d_1$ that is smaller than the diameter, d, of the beads 110. An expansion step 404 is then executed to increase the diameter of the expandable wells 308. FIG. 4C shows the testing device 300 following the expansion step 404, which has created a matrix of expanded wells 408, each having a second selected well diameter $d_2$ that exceeds the selected first well diameter $d_1$. In a bead introduction step 405, the beads 110 are introduced onto the selectively deformable surface 304 of the selectively deformable substrate 302. Alternatively, the beads may be introduced prior to the expansion step 404. A liquid medium may or may not be used during the bead loading procedure 400. FIG. 4D shows the DNA testing device 300 after introduction of the beads 110. It can be advantageous for the selected second well diameter $d_2$ to remain slightly smaller than the bead diameter d, so that the beads 110 easily fall partially into the expandable wells 308. It can also be advantageous for the physical density (i.e., mass per unit volume) of the beads to exceed the density of a liquid medium that can be used during the loading procedure, so that the beads 110 displace the medium and seat themselves more solidly in the expandable wells 308.

Next, it may be beneficial to position the array to encourage bead capture. For example, mechanically vibrating the selectively deformable substrate 302 during a vibration step 406, may assist the beads 110 in self-centering within the expandable wells 308. Alternatively, depending on the construction of the testing device 300, the selectively deformable surface 304 may be capable of vibrating relative to the substrate 302. Vibrations can be introduced by an external mechanical source that imparts energy directly or indirectly to either the substrate 302, the selectively deformable surface 304, or the testing device 300 as a whole.

FIG. 4F shows the testing device 300 after the beads 110 are seated in the expanded wells 408, after which time the selectively deformable substrate 302 can be manipulated in a contraction step 407 so as to reduce the diameter of the expanded wells 408 to a selected third well diameter $d_3$ that is smaller than the selected second well diameter $d_2$, causing the wells to contract around the seated beads 110. Electrical excitation may or may not be needed for the contraction step 407. The beads 110 can be held in place by mechanical forces within the contracted wells 418, not only by radial pressure from the sides of the contracted wells 418, but also by polymeric surface friction. Although there may still exist some unoccupied wells 418 following the loading procedure 400, the array produced in the selectively deformable substrate 302 is likely to become more uniformly filled than the rigid microarray platform 106. In one embodiment, the vibrations mentioned above can take the form of repeated expansions and contractions of the selectively deformable substrate 302.

Figure 5A:
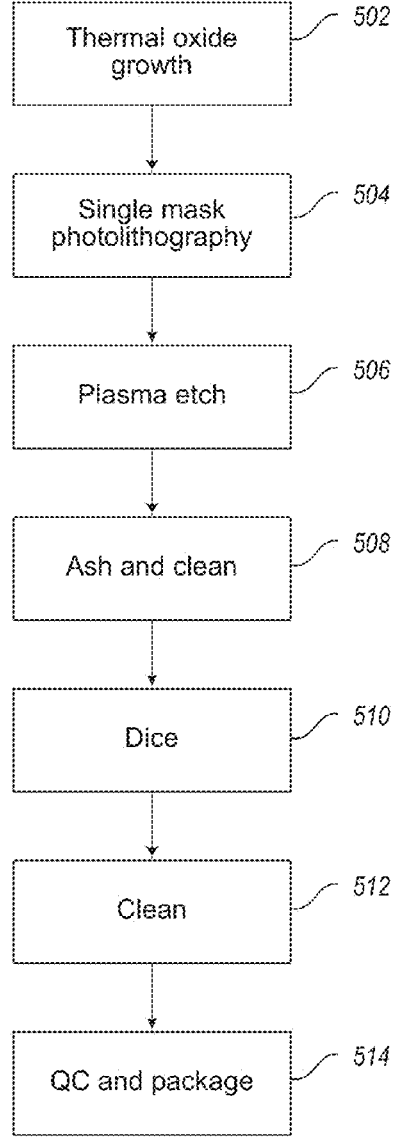
FIGS. 5A-5E show a sequence of steps and corresponding side views illustrating a typical method of fabricating a microarray according to the prior art.
Figure 5B:
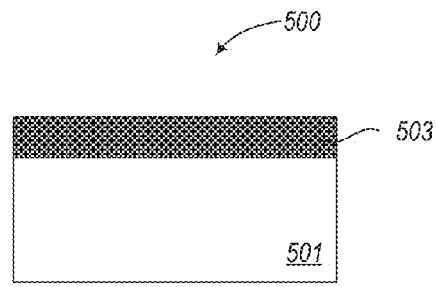
Figure 5C:
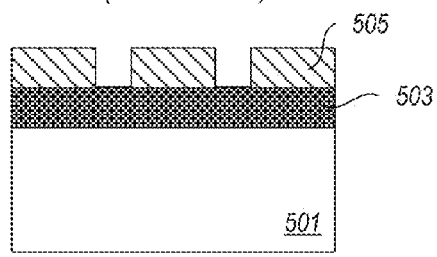
Figure 5D:
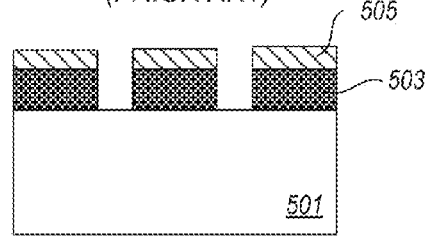
Figure 5E:
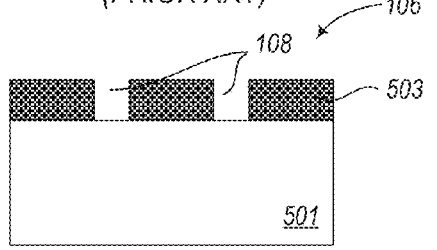

FIGS. 5A-5E, 6A-6C, and 7A-7D pertain to methods of making testing platforms. FIG. 5A shows an exemplary typical process sequence 500 of processing steps that can be used to create the conventional rigid microarray platform 106 on a silicon substrate 501. In an oxide formation step 502, a blanket layer of silicon dioxide ($SiO_2$) 503 is formed (e.g., grown) on the silicon substrate 501 (FIG. 5B). In a lithography step 504 a single lithography spin-expose-develop masking sequence is performed. The lithography step 504 includes spinning a layer of photosensitive polymer (e.g., photoresist) onto the blanket oxide layer 503, exposing the photoresist to light through a reticle containing a specified matrix pattern of wells 108, and developing away the exposed regions of photoresist to create a well matrix pattern that can be used as a photoresist mask 505 (FIG. 5C). In an etching step 506, the photoresist mask 505 is used to transfer the well matrix pattern to the underlying blanket oxide layer 503 by etching exposed areas of the oxide layer 503 to creating a well matrix patterned oxide layer 507 on the surface of the silicon substrate 501 (FIG. 5D). Following the etching step 506, remaining photoresist is removed in an ash/clean sequence 508 to yield the resulting microarray (FIG. 5E). The finished well matrix patterned oxide layer 507 forms the rigid glass surface of the conventional rigid microarray platform 106.

FIG. 6A shows an example of a first process sequence 600 of processing steps that can be used to create the testing device 300 featuring the selectively deformable surface 304. The first process sequence 600 begins with a conventional silicon substrate 601, similar to the silicon substrate 501. In step 602, a surface treatment can be performed, for example, to remove a native oxide that can spontaneously grow on the silicon surface, e.g., when the silicon surface is exposed to air or another oxygenated environment (FIG. 6B). The surface treatment in step 602 can be, for example, a plasma cleaning treatment performed in a vacuum chamber, a wet chemical dip such as a mixture of sulfuric acid and hydrogen peroxide ("pirhana bath"), or a buffered oxide etch (BOE) that contains hydrofluoric acid (HF), or a chemical spray treatment. Removal of native oxide tends to improve adhesion of materials to the silicon surface. In addition to removal of a native oxide, other or additional surface treatments performed as part of the step 602 can use alternative methods to promote better adhesion to the silicon surface of a subsequent layer of material. Techniques to increase adhesion of a subsequent next layer include, among others, roughening the surface, making the surface porous, depositing an adhesion-promoting layer, and adding adhesion-promoting chemical formulations to the next layer material. A prolonged HF treatment, for example, can be used to make the surface porous. Surface roughening can also be achieved with a ballistic process such as an argon plasma processing step. It is generally advantageous to use a surface treatment in step 602 instead of depositing a special adhesion layer or adding adhesion promoters to the next layer material.

Step 604 is an optional metallization step that can be performed if a circuit pattern is to be placed adjacent to the selectively deformable surface 304 so that, during the loading procedure, characteristics of the excitation can be made well-specific, or specific to a group or sub-matrix of wells. Using this optional step 604, it is possible to integrate different matrices of wells with different testing criteria on a single testing device 300. In one embodiment, a patterned metal layer 605 for directing electrical excitation signals to influence specific ones, or groups, of the expandable wells 308 can be inserted between the silicon substrate 601 and the selectively deformable surface 304, as shown in FIG. 6C. The metal pattern may be designed so as to place metal at the bottom of one or more wells 308, as shown, or alternatively, for example, to place metal near the corners of one or more wells, without extending metal across the bottoms of the wells. In another embodiment, a patterned metal layer for controlling a particular sub-matrix of wells can be inserted between the silicon and the polymer, as shown in FIG. 6D. For example, a first region of metal 605a, in FIG. 6D, is shown adjacent to a polymer submatrix 304a that includes the well 308a, while a second region of metal, 605b, in FIG. 6D is shown adjacent to a polymer submatrix 304b that includes the well 308b. The first region of metal 605a then can influence a first population of nanocomposite elements embedded in the polymer submatrix 304a, while the second region of metal 304b can (e.g., differently) influence a second population of nanocomposite elements that are embedded in the polymer submatrix 304b.

In other embodiments, a layer of another, non-metallic, material can be substituted for the metallization layer 605, for example, a semiconducting material such as polysilicon or a doped polysilicon. Such a material, even though it is not strictly metallic, can still be capable of transmitting signals by conduction or capacitive coupling to influence some wells differently from others.

Because the desired result is a flexible polymeric surface instead of a rigid surface, formation of a silicon dioxide layer 503 used in the typical sequence 500 is not relevant. Instead, a matrix pattern of the expandable wells 308 is simply formed in the photoresist itself, during the single mask photolithography step 606. In place of a conventional photoresist, a special bio-compatible, photo-sensitive, and selectively deformable polymer is used, that has physical properties subject to influence by external forces. The selectively deformable polymer can be spun directly onto the silicon substrate 601 to create the selectively deformable surface 304. As discussed above, the surface treatment in step 602 can promote better adhesion of the selectively deformable surface 304 (or, if used, the metal layer 605) to the silicon surface, thereby eliminating the need of either an adhesion promoting layer, or an adhesion promoting treatment during the photolithography step 606.

The selectively deformable surface 304, being translucent, can then be exposed through a reticle containing a specified matrix pattern to form expandable wells 308. Ultraviolet (UV) light can be used during the exposure step. Developing away the exposed regions of the polymer creates the desired well matrix pattern in the selectively deformable surface 304, or 304a and 304b (see FIGS. 6C and 6D, including optional metallization, and FIG. 6E, without optional metallization). Depending on the photosensitive properties of the deformable surface 304, the well matrix pattern may alternatively be formed by developing away unexposed regions of the selectively deformable surface 304. In other words, the polymer material used may act as either a positive or a negative photoresist. The intensity of the UV light and the exposure duration can be varied to optimize the shape of the well profile. Furthermore, if desired, striations can be incorporated into the reticle design, and/or striations can be a characteristic feature of the deformable polymer, so as to deliberately form a ridged profile in the polymer. Whereas striations in photoresist are usually considered detrimental, their effect on the deformable polymer is to produce an improved well profile that has a beneficial gripping surface to facilitate bead capture and retention.

There is no need for etch, ash, and clean steps in the first process sequence 600. At this point, formation of the selectively deformable substrate 302 is complete. An optional post-processing surface treatment can be performed in step 608, for example, to ensure bio-compatibility, based on the particular experimental application, or to eliminate surface residue, polymer debris, or other contaminants remaining on the polymeric surface 304. The post-treatment step 608 can also be used to adjust porosity or a hydrophyllic characteristic of the polymeric surface 304. A water wash or an isopropyl alcohol (IPA) clean, for example, can be used in step 608. The post-treatment step 608 can include other chemical treatments or physical processes such as an argon/oxygen plasma treatment to make the selectively deformable surface 304 either hydrophyllic or hydrophobic, to a permissible and/or a required degree, as needed for bio-compatibility of the surface, based on the experimental application. The substrate can then be cut into individual arrays (step 610), and cleaned again (step 612), before final test and packaging (step 614).

In another embodiment, a second process sequence 700 for fabricating the test device 300 having expandable wells 308, starting with a silicon substrate 701, is shown in FIGS. 7A-7D. The silicon substrate 701 employed here optionally can contain pre-fabricated electrical components (e.g., transistors) or circuits instead of, or in addition to, (e.g., underlying) those provided for excitation of the deformable polymer. According to the second process sequence 700 shown in FIG. 7A, an initial silicon surface treatment (step 702; FIG. 7B) can be performed, after which any number of layers, used to build optional underlying circuitry 703 may be optionally deposited and patterned prior to introducing the selectively deformable polymer. The optional underlying circuitry 703 can include transistors and associated interconnects (e.g., a multi-layer metal interconnect structure), patterned either on the front side, as shown in FIGS. 7C and 7D, or on the back side, of the silicon substrate 701. A single mask lithography step 706 is then added to the second process sequence 700 in similar fashion to the single mask photolithography step 606, that involves coating the substrate with a photosensitive, selectively deformable polymer 304 (FIG. 7C) and patterning the polymer (FIG. 7D). A post-processing surface treatment 708, similar to the post-processing step 608, is also optional. If the optional steps are omitted from the sequences 600 and 700, it is possible to form the array of wells 308 using only one single mask lithography step, after which the testing device 300 is complete and ready for the standard dice (710), clean (712), and packaging (714) steps.

Both the first process sequence 600 and the second process sequence 700 have the advantage of simplicity when compared with the typical process sequence 500, because the oxide layer is entirely omitted. Thus, the manufacture of the testing device 300, having expandable wells 308 formed directly in the selectively deformable surface 304, is both more efficient and less expensive than the manufacture of the rigid microarray platform 106, while offering greater capability.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of making a testing device suitable for genetic experimentation, the method comprising:
   forming on a substrate a selectively deformable surface exhibiting a piezoelectric property that causes the selectively deformable surface to respond mechanically to electrical excitation; and
   forming a matrix of wells in the selectively deformable surface suitable to capture and retain a plurality of beads, the matrix of wells expanding to accept placement of a bead in each well and contracting to secure the bead in the well in response to an applied electric field.

2. The method of claim 1, wherein the forming further comprises patterning the selectively deformable surface using a photolithography technique.

3. The method of claim 1, wherein the mechanical response varies depending on a selected electrical excitation.

4. The method of claim 1, wherein forming the selectively deformable surface includes coating the surface with a photosensitive bio-compatible polymer.

5. The method of claim 4, further comprising, before coating the surface, performing a surface treatment to modify adhesion properties of the surface.

6. The method of claim 5, wherein the surface treatment removes native oxide from the substrate.

7. The method of claim 5, wherein the surface treatment increases porosity of the surface.

8. The method of claim 5, wherein the surface treatment includes a ballistic process.

9. The method of claim 4, wherein the polymer includes striations.

10. The method of claim 4, further comprising a polymer surface post-treatment to adjust a hydrophyllic quality of the polymer surface.

11. The method of claim 4, further comprising a polymer surface post-treatment to adjust a hydrophobic quality of the polymer surface.

12. The method of claim 4, further comprising inserting a signal transmission layer adjacent to the polymer, the signal transmission layer capable of accessing one or more subsets of wells.

13. A testing device suitable for genetic experimentation, comprising:
  a substrate having a selectively deformable surface;
  piezomagnetic sensing elements incorporated within the selectively deformable surface, the piezomagnetic sensing elements responsive to magnetic excitation; and
  a matrix of wells formed in the selectively deformable surface that expand to accept placement of a bead in each well and contract to secure the bead in the well, via motion of the piezomagnetic sensing elements in response to an applied magnetic field.

14. The device of claim 13, further comprising a signal transmission layer formed adjacent to the selectively deformable surface, which signal transmission layer transmits electrical signals that influence selected piezoelectric sensing elements dispersed throughout the selectively deformable surface.

15. The device of claim 13, wherein the well retains the bead by mechanical forces associated with contraction of the well.

16. A testing device suitable for genetic experimentation, comprising:
  a substrate having a selectively deformable surface
  a matrix of wells formed in the selectively deformable surface;
  piezoelectric sensing elements incorporated into the selectively deformable surface
  expansion means for accepting placement of a bead into a well; and
  contraction means for securing the bead in the well, the expansion means and contraction means involving electrical excitation of the piezoelectric sensing elements.

17. The testing device of claim 13, wherein the selectively deformable surface is made of a biocompatible, photosensitive polymer.

18. The testing device of claim 13 wherein the piezoelectric sensing elements are nanocomposite elements.

19. The testing device of claim 13 wherein the nanocomposite elements are made of zinc oxide.

20. A testing device suitable for genetic experimentation, comprising:
  a substrate having a selectively deformable surface;
  piezomagnetic sensing elements incorporated within the selectively deformable surface, the piezomagnetic sensing elements responsive to magnetic excitation; and
  a matrix of wells formed in the selectively deformable surface that expand to accept placement of a bead in each well and contract to secure the bead in the well, via motion of the piezomagnetic sensing elements in response to an applied magnetic field.

21. The testing device of claim 20, further comprising a signal transmission layer formed adjacent to the selectively deformable surface, wherein the signal transmission layer transmits magnetic signals that influence piezomagnetic sensing elements within selected regions of the selectively deformable surface.

22. The testing device of claim 21, wherein the signal transmission layer is made of a semiconducting material.

* * * * *

UNITED STATES PATENT AND TRADEMARK OFFICE
CERTIFICATE OF CORRECTION

| | | |
|---|---|---|
| PATENT NO. | : 8,906,696 B2 | Page 1 of 1 |
| APPLICATION NO. | : 13/593319 | |
| DATED | : December 9, 2014 | |
| INVENTOR(S) | : Archit Giridhar | |

It is certified that error appears in the above-identified patent and that said Letters Patent is hereby corrected as shown below:

IN THE CLAIMS

Column 11, Line 20:
"piezomagnetic sensing elements incorporated within the" should read, --piezoelectric sensing elements incorporated within the--.

Column 11, Lines 21-22:
"selectively deformable surface, the piezomagnetic sensing elements to responsive to magnetic excitation" should read, --selectively deformable surface, the piezoelectric sensing elements responsive to electric excitation--.

Column 11, Line 26-27:
"motion of the piezomagnetic sensing elements in response to an applied magnetic field." should read, --motion of the sensing elements in response to an applied electric field.--.

Column 11, Line 39:
"a substrate having a selectively deformable surface" should read, --a substrate having a selectively deformable surface;--.

Column 12, Line 4:
"selectively deformable surface" should read, --selectively deformable surface;--.

Signed and Sealed this
Twenty-second Day of December, 2015

Michelle K. Lee
*Director of the United States Patent and Trademark Office*